United States Patent [19]

Gidda et al.

[11] Patent Number: 4,920,102
[45] Date of Patent: Apr. 24, 1990

[54] METHOD FOR TREATING GASTROINTESTINAL DISORDERS

[75] Inventors: Jaswant S. Gidda, Carmel; Herbert A. Kirst, Indianapolis; David W. Robertson, Greenwood, all of Ind.

[73] Assignee: Eli Lilly and Company, Indianapolis, Ind.

[21] Appl. No.: 182,645

[22] Filed: Apr. 18, 1988

[51] Int. Cl.$^5$ .................. A61K 31/70; C07H 17/08
[52] U.S. Cl. ............................... 514/28; 536/7.1; 536/7.2
[58] Field of Search ............ 536/7.1, 7.2; 514/30, 514/28, 29

[56] References Cited

U.S. PATENT DOCUMENTS

| 4,547,491 | 10/1985 | Mrozik et al. | 536/7.1 |
| 4,677,097 | 6/1987 | Omura et al. | 514/29 |

FOREIGN PATENT DOCUMENTS 0215355  3/1987  European Pat. Off.

OTHER PUBLICATIONS

Z. Itoh et al., "Erythromycin Mimics Exogenous Motilin in Gastrointestinal Contractile Activity in the Dog," Am. J. Physiol. 247, G688–694, (1984).
M. A. Pilot et al., "Alterations in Gastrointestinal Motility Associated with Erythromycin," Brit. J. Pharmacolog. 81, 168P, (1984).
S. Omura et al., "Gastrointestinal (GI) Motor-Stimulating Activity of Erythromycin Derivatives," Interscience Conference on Antimicrobial Agents and Chemotherapy (ICCAAC) meeting, 1985.
S. Omura et al., "Gastrointestinal Motor-Stimulating Activity of Macrolide Antibiotics and the Structure-Activity Relationship", J. Antibiotics 38 (11), 1631–1632, (1985).
S. Omura et al., "Macrolides with Gastrointestinal Motor Stimulating Activity," J. Med. Chem 30 (11), 1941–1943, (1987).
S. Omura, "Motilide, A Series of Macrolides with Gastrointenstinal Motor Stimulating Activity," Abstract from Japanese-U.S. Congress of Pharmaceutical Sciences Meeting, 1987.
B. L. Carter, et al., "Gastrointestinal Side Effects with Erythromycin Preparation," Drug. Intell. & Clin. Pharmacy 21, 734–738, (1987).
Z. Itoh et al., "Gastrointestinal Motor-Stimulating Activity of Macrolide Antibiotics and Analysis of Their Side Effects on the Canin Gut," Antimicrob Ag. Chemotherap. 26 (6), 863–869, (1984).
Z. Itoh et al., "Structure-Activity Relation Among Macrolide Antiobiotics in Initiation of Interdigestive Migrating Contractions in the Canine Gastrointestinal Tract", Am. J. Physiol. 248, G320–G325, (1985).
X. Y. Qin, et al., "Comparison of the Side Effects and Gastrointestinal Motility Observed after Administration of Erythromycin and Josamycin to Dogs," J. Antimicrob. Chemotherapy 18, 747–756, (1986).
M. A. Pilot, et al., "Macrolides and Gastrointestinal Motility," ibid. 22, Suppl. B, 201–206, (1988).
T. Tomomasa, et al., "Erythromycin Induces Migrating Motor Complex in Human Gastrointestinal Tract," Digestive Diseases & Sciences 31 (2), 157–161, (1986).
Z. Itoh, et al., "Motilide, A New Family of Macrolide Compounds Mimicing Motilin," Abstr., 11th Internatl. Symposium on Gastrointestinal Motility, Oxford, England, Sept. 7–11, 1987, p. 915.
Y. Kondo, et al., "Erythromycin and its Derivatives with Motilin-Like Biological Activities Inhibit the Specific Binding of $^{125}$I-Motilin to Duodenal Muscle," Biochem. Biophys. Res. Commun. 150, 877–882, (1988).
I. Depoortere, et al., "Macrolinde Antiobiotics are Motiling Receptor Agonists," Heptao-Gastroenterol, 35, 198, (1988).
T. Nakayoshi, et al., "Comparative Study of Effects of 14–and 16–Membered Macrolides on Gastrointestinal Motility in Unanesthetized Dogs," Drugs Exptl. Clin. Res. 14 (5), 319–325, (1988).
Y. Tanaka, et al., "Radioimmuno Assay for Erythromycin Derivatives," J. Antibiotics 41 (2), 258–260, (1988).
I. O. Kibwage, et al., "Translactionization in Erythromycin," J. Org. Chem. 52, 990–996, (1987).
I. O. Kibwage, et al., "Identification of Novel Erythromycin Derivatives in Mother Liquor Concentrates of Streptomyces Erythraeus," J. Antibiotics 40 (1), 1–6, (1987).
H. A. Kirst, et al., "Synthesis of Ring-Contracted Derivatives of Erythromycin," J. Org. Chem. 52, 4359–4362, (1987).
S. N. Heyman et al., "Erythromycin-Induced Dynamic Ileus?" J. Clin. Gastrointerol 10 (4), 551–554, (1988).
Kitasato Kenkyusho, Derivent Abstract 87-066334/10, Abstracting EPO Application 213,617A, "Digestive Tract Contractile Motion Stimulent with Low Toxicity Comprises Erythromycin A, B, C, D or E Deriv."

Primary Examiner—John W. Rollins
Assistant Examiner—Elli Peselev
Attorney, Agent, or Firm—Nancy J. Harrison; Leroy Whitaker

[57] ABSTRACT

Novel ring-contracted macrolides which enhance gastrointestinal motility and novel methods and compositions for treating gtastrointestinal disorders in animals with these macrolides and with certain other previously known ring-contracted macrolides are provided.

24 Claims, No Drawings

METHOD FOR TREATING GASTROINTESTINAL DISORDERS

SUMMARY OF THE INVENTION

This invention provides novel methods for treating gastrointestinal disorders in animals. These methods comprise administering to the animal an amount of a ring-contracted macrolide of formula 1

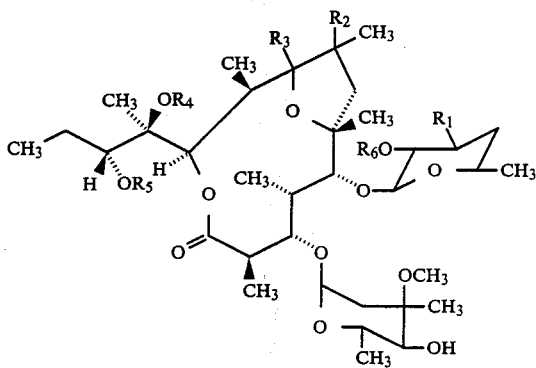

wherein $R_1$ is $-N(CH_3)_2$ or $-[N(CH_3)_2R]^+X^-$;

R is $C_1$-$C_6$-alkyl, $C_2$-$C_6$-alkenyl, $C_2$-$C_6$-alkynyl, benzyl or benzyl substituted by from 1 to 3 substituents selected from fluoro, chloro, $C_1$-$C_4$-alkyl, $C_1$-$C_4$-alkoxy, nitro, $C_1$-$C_4$-alkoxycarbonyl, $-N(C_1$-$C_4$-alkyl$)_2$ or cyano;

$R_2$ and $R_3$ are H or together form a single bond;

$R_4$ and $R_5$ independently are H or $C_1$-$C_4$-acyl, or together with a carbonyl group form a five-membered cyclic carbonate;

$R_6$ is H or $C_1$-$C_4$-acyl; and $X^-$ = halide, hydroxide, carboxylate, sulfate, phosphate, nitrate, $C_1$-$C_3$-alkylsulfonate or arylsulfonate (such as p-toluenesulfonate or benzenesulfonate);

or, when $R_1 = -N(CH_3)_2$, a pharmaceutically acceptable salt thereof; which enhances gastrointestinal motility.

The subgroup of formula 1 compounds which excludes the compounds wherein (1) $R_1 = -N(CH_3)_2$; (2) $R_2$ and $R_3$ = a single bond and (3) $R_4$ and $R_5$ = H are novel macrolides derived from erythromycin (1a compounds). The 1a compounds and pharmaceutical formulations for treating gastrointestinal disorders which comprise as an active ingredient a formula 1 compound, or a pharmaceutically acceptable salt of those 1 compounds wherein R $= -N(CH_3)_2$, are also part of this invention.

DETAILED DESCRIPTION OF THE INVENTION

Background of the Invention

The gastrointestinal tract transports ingested food material from oral to aboral direction in a well coordinated fashion. Transport is brought about by peristaltic contractions of the circular muscle layers. Coordination of the transport is accomplished by integrated central and peripheral nervous inputs.

Defects in the normal motility pattern can lead to development of aperistalsis, enhanced transit, gastrointestinal stasis (such as that seen in diabetic gastroparesis) or to an adynamic ileus. One prevalent defect, when lower esophageal sphincter tone is low, causes retrograde propulsion of stomach contents into the esophagus. This problem can lead to the development of esophagitis.

The exact pathophysiology of motility disorders is not well understood. Consequently, a rational therapy for treating these disorders is also not available. Pharmacological agents which enhance the motility in the paralytic gut may have usefulness in the treatment of diseases such as dyspepsia, gastroparesis, gastroesophageal reflux disease and surgery-induced adynamic ileus. Additionally, motility-enhancing agents (also called gastroprokinetic agents) may facilitate the placement of diagnostic instrumentation in the gastrointestinal tract.

Currently, metoclopramide, a benzamide with dopamine D2-receptor antagonist activity, is the only drug approved in the United States for treating motility disorders. Unfortunately, metoclopramide has several side effects, which range from prolactin increase to development of dyskinesia, etc. Thus, the need for a potent, selective, efficacious and safe drug to treat gastrointestinal motility disorders is great.

Since the introduction of macrolide antibiotics clinically, it is known that they can cause abdominal cramps and diarrhea. Whether these side effects are secondary to their antibiotic activity or are due to their effect on gastrointestinal motility and secretion is not known. Recently, Omura et al. chemically modified erythromycin in an attempt to find compounds with improved gastroprokinetic properties, but negligible antibacterial activity (See *J. Med. Chem.* 30(11):1941-1943, 1987; *J. Antibiotics* 38(11):1631-1632, 1987; Ther. in 21st Cent. Jap. U.S. Cong. Pharm. Sci. abstract #14, 1987; Interscience Conf. Antimicrob. Agents & Chemotherapy, abstract #1149, 1985). Omura's group reported that several of the compounds they prepared showed gastroprokinetic potency greater than that of erythromycin. The in vitro activity of the most potent of these compounds, however, was not inhibited by nerve blocking agents (tetrodotoxin, TTX) or by a cholinergic muscarinic antagonist (atropine).

We have discovered a new group of erythromycin derivatives, i.e. the formula 1 compounds, which are both chemically and biologically different from those reported by Omura et al. The formula 1 compounds enhance gastrointestinal motility through the cholinergic mechanisms which are primarily utilized by the normal gut. This mechanism of action is demonstrated by the fact that the gastrointestinal motility enhanced by the formula 1 compounds was blocked by atropine (30 μg/kg). In addition, these potent gastroprokinetic macrolides have the desirable feature of having minimal antibiotic activity.

As used herein, the term "alkyl" includes straight, branched and cyclic hydrocarbon moieties and combinations thereof containing the specified number of carbon atoms.

The terms "alkenyl" and "alkynyl" refer to those alkyl groups which contain from 1 to 2 double and/or triple bonds. The double bonds can be in either the cis or trans configuration.

The term "$C_1$-$C_4$-acyl" refers to an acyl moiety derived from a carboxylic acid containing from one to four carbon atoms.

The term "halide" means chloride, bromide or iodide.

The term "carboxylate" refers to the anion of an organic carboxylic acid such as acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Certain derivatives of this invention form salts, particularly acid addition salts. These acid addition salts are also useful as gastroprokinetic agents and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric and the organic acids listed supra.

Pharmaceutically acceptable acid addition salts are an especially preferred group of salts of this invention. Pharmaceutically acceptable acid addition salts are those salts useful in the chemotherapy of a warm-blooded animal.

Typical formula 1 compounds are shown in Table I.

TABLE I
Illustrative Formula 1 Compounds

| Compound Number | $R_1$ | $R_2$ | $R_3$ | $R_4$ | $R_5$ | $X^c$ |
|---|---|---|---|---|---|---|
| 1 | $-N(CH_3)_2$ | | $db^a$ | H | H | — |
| 2 | $-N(CH_3)_2$ | | db | $-C(=O)^b-$ | | — |
| 3 | $-N(CH_3)_2$ | H | H | H | H | — |
| 4 | $-N(CH_3)_2$ | H | H | $-C(=O)-$ | | — |
| 5 | $-N(CH_3)_3^+$ | | db | H | H | I |
| 6 | $-N(CH_3)_2(CH_2C\equiv CH)^+$ | | db | H | H | Br |
| 7 | $-N(CH_3)_2(CH_2CH=CH_2)^+$ | | db | H | H | Br |
| 8 | $-N(CH_3)_2[CH_2C(CH_3)=CH_2]^+$ | | db | H | H | Cl |
| 9 | $-N(CH_3)_2[(CH_2)_3CH_3]^+$ | | db | H | H | Br |
| 10 | $-N(CH_3)_3^+$ | H | H | H | H | I |
| 11 | $-N(CH_3)_3^+$ | H | H | $-C(=O)-$ | | I |
| 12 | $-N(CH_3)_3^+$ | | db | $-C(=O)-$ | | $\frac{1}{2}SO_4$ |
| 13 | $-N(CH_3)_2(CH_2C\equiv CCH_3)^+$ | | db | H | H | OTs |
| 14 | $-N(CH_3)_2(CH_2C\equiv CH)^+$ | H | H | H | H | OMs |
| 15 | $-N(CH_3)_2(CH_2C\equiv CH)^+$ | | db | Ac | Ac | OAc |
| 16 | $-N(CH_3)_2CH_2Ph^+$ | | db | H | H | Br |

$^a R_2$ and $R_3$ together form a bond
$^b R_4$ and $R_5$ together with a corbonyl group form a 5-membered cyclic carbonate
$^c$ Ts = tosylate; Ms = mesylate; and Ac = acetate Pharmaceutical formulations for the treatment of gastrointestinal disorders comprising a formula 1 compound or a pharmaceutically acceptable salt of those I compounds wherein $R_1=-N(CH_3)_2$ are also part of this invention. The compounds can be formulated for oral or parenteral administration for the therapeutic or prophylactic treatment of gastrointestinal motility disorders. For example, a compound of this invention can be admixed with conventional pharmaceutical carriers and excipients and used in the form of tablets, capsules, elixirs, suspensions, syrups, wafers and the like. The compositions comprising a compound of this invention will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the compound can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained release or enterically coated preparations may also be devised. For pediatric and geriatric applications, suspensions, syrups and chewable tablets are especially suitable.

Alternatively, the unit dosage form of the compound can be a solution of the compound in a suitable diluent in sterile, hermetically sealed ampoules. The concentration of the compound in the unit dosage may vary, e.g. from about 1 percent to about 50 percent, depending on the compound used and its solubility and the dose desired by the physician.

In a further aspect, this invention provides a method for treating gastrointestinal motility disorders in animals. The term "treating" is used to denote both prevention of the disorder and control of the disorder after the host animal has become afflicted. The method comprises administering to the animal an effective dose of a compound of this invention. An effective dose is generally between about 0.02 and about 100 mg/kg of the compound or its pharmaceutically acceptable salt. A preferred dose is from about 0.05 to about 50 µg/kg of compound. A typical daily dose for an adult human is from about 50 mg to about 0.5 g.

In practicing this method, the compound compound can be administered as a single daily dose or in multiple doses per day. The treatment regime may require administration over extended periods of time, e.g., for several days or for several weeks. The amount per administered dose or the total amount administered will depend on such factors as the nature and severity of the problem and the age and general health of the patient. A convenient method of practicing the treatment method is to administer the compound orally, using tablets, capsules, suspensions, syrups and the like. The compound may also be administered by other methods, e.g. as a suppository or parenterally via IV infusion.

We provide the following non-limiting examples in order to illustrate this invention.

Product purification by chromatography was performed on silica gel, using either flash chromatography techniques (E. Merck grade 60 silica gel, 230-400 mesh) or a Waters Model 500 Prep LC system.

Compounds were purified to homogeneity according to thin layer chromatographic (TLC) and proton NMR analyses.

PREPARATION 1

8,9-Anhydro-erythromycin-6,9-hemiketal

A solution of erythromycin (20.0 g, 27.3 mmol) in glacial acetic acid (100 ml) was stirred at room temperature for 1 hour. Sodium hydroxide (5N) was slowly added in portions. After each addition, the mixture was allowed to return to ambient temperature. After precipitation was complete, the mixture was extracted twice with dichloromethane. The combined organic layers were extracted with saturated sodium bicarbonate solution, dried (sodium sulfate), filtered and evaporated. The crude produce (18.9 g) was purified by preparative HPLC (linear gradient of dichloromethane to 7% methanol +0.5% ammonium hydroxide in dichloromethane) to yield the title compound (13.2 g, 68%) as a white solid.

PREPARATION 2

Preparation of Compound 1

8,9-Anhydro-erythromycin-6,9-hemiketal (10.0 g, 14 mmol) in methanol (200 mL) was treated with potassium carbonate (1.9 g, 14 mmol), and the mixture was refluxed for 90 min. Solvent was evaporated under reduced pressure, and the residue was partitioned between dichloromethane and saturated sodium bicarbonate solution. The organic layer was evaporated to give 9.6 g of a white foam. This foam was purified by preparative HPLC (linear gradient of dichloromethane to 7.5% methanol +0.5% ammonium hydroxide in dichloromethane) to yield Compound 1 (5.4 g, 54%) as a white solid. FDMS $m/e$ 715 (M+H).

EXAMPLE 1

A. Activity of the Compounds

Methods

Motility in the stomach and duodenum was recorded using standard techniques (P. Bass and J. N. Wiley, Am. J. Physiol. 208:908-913, 1965). Briefly, ferrets of either sex, weighing 1.0-1.5 kg were anesthetized by pentobarbital (30 mg/kg, i.p.). Anesthesia was maintained by injecting pentobarbital as a bolus dose (5 mg/kg, i.v.) as required. All animals were allowed to breath spontaneously through a tracheal tube. The jugular artery and vein were cannulated to record blood pressure and inject test substances. Body temperature was maintained using a heated water jacket. An abdominal incision was made to expose the stomach and proximal duodenum. Strain gauges (R. B. Products, Wisconsin) were sewn on the serosal surface of the stomach and duodenum 2 cm proximal and 2 cm distal to the pyloric sphincter, respectively. The strain gauges were oriented to record the force development in the circular muscle layer only, because the contractile activity of this muscle layer results in the propulsion of ingested food material. The abdominal cavity was closed with a towel clamp, and the output of strain gauge was displayed on a dynograph strip chart recorder.

The drugs were dissolved in 50% DMSO and were made fresh every day. The bolus injection was given rapidly and the i.v. line was flushed following the drug injection with ½ cc of physiological saline. A minimum 5-min. period was allowed between doses. However, if motility did not return to the pretreatment level, more time was allowed, but the time did not exceed 10 minutes. At the end of the experiment the animals were euthanized with a bolus dose of T-61 (1 cc).

Data Analysis

The number and amplitude of contractions in the one-min. period following the bolus injection were manually calculated. The amplitude of all responses was averaged and is reported as grams of tension developed/minute. No statistical analysis was performed. Most of the compounds were tested at a screening dose of 10 µg/kg. However, a dose-response curve for the lead compound was determined.

Results

Table II shows the effect of illustrative formula 1 compounds on the tension developed in the circular muscle layers of the stomach:

TABLE II:

| | Effect of Formula 1 Compounds on Gastrointestinal Motility | |
|---|---|---|
| Compound[a] | Dose (IV, µg/kg) | Tension Developed (g/min.) |
| Erythromycin | 100 | 1.40 |
| 1 | 7 | 1.40 |
| 1 | 10 | 2.15 |
| 1 | 30 | 3.45 |
| 2 | 20 | 2.95 |
| 5 | 10 | 6.97 |
| 6 | 20 | 1.80 |

[a]Compound numbers from Table I

EXAMPLE 2

A. Preparation of Compound 2

A solution of erythromycin enol ether (500 mg, 0.7 mmol) and ethylene carbonate (1.0 g, 11.4 mmol) in 1,2-dimethoxyethane (25 mL) was treated with $K_2CO_3$ (500 mg, 3.6 mmol). The resulting mixture was heated to reflux with the exclusion of moisture. After 19 hours, an additional portion of ethylene carbonate (500 mg, 5.7 mmol) was added to the reaction, and heating was continued for 7 hours. The mixture was diluted with $CH_2Cl_2$ (50 mL) and extracted with $H_2O$ (3×100 mL). The $CH_2Cl_2$ solution was dried ($Na_2SO_4$) and evaporated to dryness. The residue was chromatographed on a silca-gel flash column, using a 1-L gradient of CH2Cl2 to CH2Cl2/MeOH/NH<OH (92.5:7.5:0.5), followed by 1 L of the latter solvent, to give two products. The higher Rf product, 92 mg, was identical to the carbonate of erythromycin enol ether. The second product was compound 2; yield: 215 mg.

B. Compound 2

IR(CHCl3): 1796, 1727 cm$^{-1}$ $^1$H NMR(CDCl3): δ5.19 (d, H-11), 4.16 (dd, H-13 overlapped with H-3), 1.58 and 1.56 (2s, 8-Me and 12-Me).

FDMS: m/e =741 (M+).

EXAMPLE 3

A Preparation of Compound 6

To Compound 1 (1.0 g, 1.4 mmoles) in chloroform (20 mL), was added 12.6 mL of 80% propargyl bromide (in toluene). The mixture was stirred at 25° for 3 hours, and the solvent was removed in vacuo. The residue was dissolved in chloroform (5 mL). Diethyl ether was added until precipitation appeared to be complete. The solid was removed by filtration and recrystallized twice (chloroform/ether). The product was dried at 25° for 18 hours to give 827 mg (70.8 %) of compound 6 as an off-white powder.

B. Compound 6

Elemental analysis [experimental (theory)]: C: 56.79 (57.55); H: 8.02 (8.21); N: 1.72 (1.68); Br: 9.39 (9.57).

FDMS m/z$^+$ 754 (M-Br), 715 (M-propargyl bromide).

$^1$H NMR (300 MHz): N(CH3)2 shift from δ 2.26 to δ 3.49 (6 protons).

EXAMPLE 4

A. Preparation of Compound 5

Compound 5 was prepared in an analogous manner to the preparation of Compound 6, starting with compound 1 (200 mg) and methyl iodide (80 μL) in chloroform (2 mL). Two recrystallizations gave 85 mg (35.4%) of the product as a tan solid.

B. Compound 5

FDMS: m/z$^+$ 730(M-1), 715 (M-CH3I), $^1$H NMR(300 MHz): N(CH3)3 δ 3.50 (9 protons).

We claim:

1. A method for treating gastrointestinal motility disorders in animals which comprises administering to the animal an amount of a compound of the formula

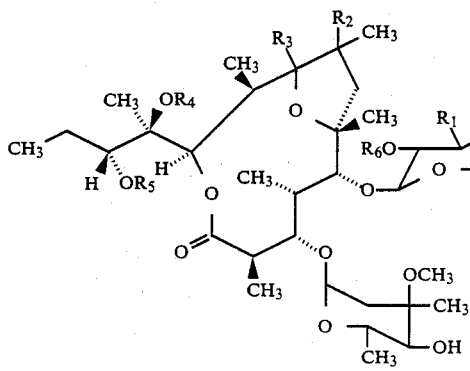

wherein

R1 is —N(CH3)2 or —[N(CH3)2R]+X$^-$;

R is C1-C6-alkyl, C2-C6-alkenyl, C2-C6-alkynyl, benzyl or benzyl substituted by form 1 to 3 substituents selected from fluoro, chloro, C1-C4-alkyl, C1-C4-alkyl, C1-C4-alkoxy, nitro, C1C4-alkoxycarbonyl, —N(C1-C4-alkyl)2 or cyano;

each one of R2 and R3 is H, or together R2 and R3 form a second single bond to make a double bond;

R4 and R5 independently are H or C1-C4-acyl, or together with a carbonyl group form a five-numbered cyclic carbonate;

R$^6$ is H or C1-C4-acyl; and

X$^-$ =halide, hydroxide, carboxylate, sulfate, phosphate, nitrate, C1-C4-alkylsulfonate or arylsulfonate;

or, when R1=—N(CH3)2, a pharmaceutically acceptable salt thereof; which is effective to enhance gastrointestinal motility.

2. A method of claim 1 wherein the compound administered is one wherein R1=—[N(CH3)2R]+X$^-$, and R and X have the meaning as defined in claim 1.

3. A method of claim 1 wherein the compound administered is one wherein R1 is —N(CH3)2.

4. A method of claim I wherein the compound administered is one wherein R2 and R3=H.

5. A method of claim 1 wherein the compound administered is one wherein R2 and R3 together form a single bond.

6. A method of claim 1 wherein the compound administered is one wherein R4 and R5=H.

7. A method of claim 1 wherein the compound administered is one wherein R4 and R5 independently are C1-C4-acyl or together with a carbonyl group form a five-membered cyclic carbonate.

8. A method of claim 5 wherein the compound administered is one wherein R1=—N(CH3)2 and R4 and R5=H.

9. A method of claim 5 wherein the compound administered is one wherein R1=—N[N(CH3)3]+ and R4 and R5=H.

10. A compound of the formula

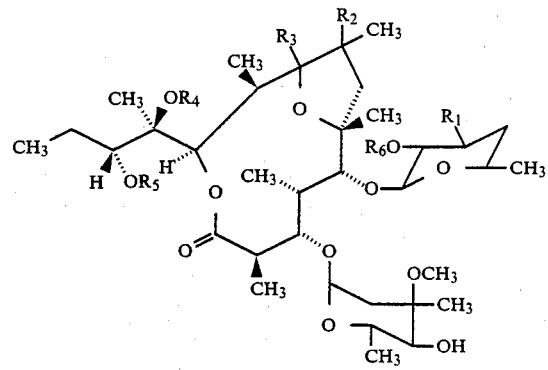

wherein

R1 is —N(CH3)2 or —[N(CH3)2RR]+X$^-$;

R is C1-C6-alkyl, C2-C6-alkenyl, C2-C6-alkynyl, benzyl or benzyl substituted by from 1 to 3 substituents selected from fluoro, chloro, C1-C4-alkyl, C1-C4-alkoxy, nitro, C1-C4-alkoxycarbonyl, —N(C1-C4-alkyl)2 or cyano;

each one of R2 and R3 is H, or together R2 and R3 form a second single bond to make a double bond;

$R_4$ and $R_5$ independently are H or $C_1-C_4$-acyl, or together with a carbonyl group form a five-membered cyclic carbonate;

$R^6$ is H or $C_1-C_4$-acyl; and $X^- =$ halide, hydroxide, carboxylate, sulfate, phosphate, nitrate, $C_1-C_3$-alkylsulfonate or arylsulfonate;

provided that, when $R_1 = -N(CH_3)_2$ and $R_2$ and $R_3$ together form a single bond, $R_4$ and $R_5$ cannot be H.

11. A compound of claim 10 wherein $R_1$ is $-[N(CH_3)_2R]^+X^-$, and R and X have the meaning as defined in claim 10.

12. A compound of claim 10 wherein R is $C_1-C_6$-alkyl.

13. A compound of claim 10 wherein R is $C_2-C_6$-alkenyl or $C_2-C_6$-alkynyl.

14. A compound of claim 10 wherein $R_1$ is $-N(CH_3)_2$.

15. A compound of claim 10 wherein $R_2$ and $R_3$ are H.

16. A compound of claim 19 wherein $R_2$ and $R_3$ together form a single bond.

17. A compound of claim 10 wherein $R_4$ and $R_5$ are H.

18. A compound of claim 10 wherein $R_4$ and $R_5$ independently are $C_1-C_4$-acyl or together with a carbonyl group from a five-membered cyclic carbonate.

19. A compound of claim 14 wherein $R_4$ and $R_5 =$ H.

20. A compound of claim 11 wherein $R_1 = -[N(CH_3)_3]^+$ and $R_4$ and $R_5 =$ H.

21. A composition useful for the treatment of gastrointestinal disorders comprising an effective amount of a compound of claim 10 with a suitable vehicle.

22. A composition useful for the treatment of gastrointestinal disorders comprising an effective amount of a compound of claim 14 with a suitable vehicle.

23. A composition useful for the treatment of gastrointestinal disorders comprising an effective amount of a compound of claim 11 together with a suitable vehicle.

24. A composition useful for the treatment of gastrointestinal disorders comprising an effective amount of a compound of claim 20 together with a suitable vehicle.

* * * * *

UNITED STATES PATENT AND TRADEMARK OFFICE
CERTIFICATE OF CORRECTION

PATENT NO. : 4,920,102
DATED : April 24, 1990
INVENTOR(S) : Jaswant S. Gidda, et. al.

It is certified that error appears in the above-indentified patent and that said Letters Patent is hereby corrected as shown below:

In Column 8 line 4, "by form" should read --by from--.

lines 5-6 "$C_1$-$C_4$-alkyl, $C_1$-$C_4$-alkyl, $C_1$-$C_4$-alkoxy" should read --$C_1$-$C_4$-alkyl, $C_1$-$C_4$-alkoxy--.

line 6, "$C_1C_4$-alkoxycarbonyl" should read --$C_1$-$C_4$-alkoxycarbonyl--.

lines 11-12, "five-numbered" should read --five membered--.

line 15, "$C_1$-$C_4$-alkylsulfonate" should read --$C_1$-$C_3$-alkylsulfonate--.

line 25, "Claim I" should read --claim 1--.

line 40, "-$N[N(CH_3)_3]^+$" should read -- $-[N(CH_3)_3]^+$ --.

line 61, "$-[N(CH_3)_2RR]^+$" should read -- $-[N(CH_3)_2R]^+$ --.

UNITED STATES PATENT AND TRADEMARK OFFICE
CERTIFICATE OF CORRECTION

PATENT NO. : 4,920,102
DATED : April 24, 1990
INVENTOR(S) : Jaswant S. Gidda, et. al.

It is certified that error appears in the above-indentified patent and that said Letters Patent is hereby corrected as shown below:

In Column 10 line 1, "Claim 19" should read --claim 10--.

Signed and Sealed this

Twenty-eighth Day of September, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,920,102
DATED : April 24, 1990
INVENTOR(S) : Jaswant S. Gidda, et al It is certified that error appears in the above-indentified patent and that said Letters Patent is hereby corrected as shown below:

Column 10, line 7, "group from" should read --group form--.

Signed and Sealed this

Fifth Day of April, 1994

*Attest:*

BRUCE LEHMAN

*Attesting Officer*    Commissioner of Patents and Trademarks